United States Patent
Zhao et al.

(10) Patent No.: US 10,634,627 B2
(45) Date of Patent: Apr. 28, 2020

(54) AUTONOMOUSLY MOBILE BACKSCATTER DETECTION APPARATUS AND METHOD, AND POSITIONING METHOD FOR THE APPARATUS

(71) Applicant: NUCTECH COMPANY LIMITED, Beijing (CN)

(72) Inventors: Ziran Zhao, Beijing (CN); Zhiqiang Chen, Beijing (CN); Dong Lin, Beijing (CN); An Cang, Beijing (CN); Jin Cui, Beijing (CN); Bin Hu, Beijing (CN); Chaoyan Zhang, Beijing (CN)

(73) Assignee: Nuctech Company Limited, Beijing (CN)

( * ) Notice: Subject to any disclaimer, the term of this patent is extended or adjusted under 35 U.S.C. 154(b) by 286 days.

(21) Appl. No.: 15/610,450

(22) Filed: May 31, 2017

(65) Prior Publication Data
US 2018/0038809 A1    Feb. 8, 2018

(30) Foreign Application Priority Data
Aug. 4, 2016 (CN) ............................ 2016 1 0634464

(51) Int. Cl.
| | |
|---|---|
| *G01N 23/203* | (2006.01) |
| *G01V 5/00* | (2006.01) |
| *A61B 5/107* | (2006.01) |
| *B25J 9/02* | (2006.01) |

(52) U.S. Cl.
CPC ........... *G01N 23/203* (2013.01); *A61B 5/107* (2013.01); *B25J 9/02* (2013.01); *G01V 5/0025* (2013.01); *G01V 5/0066* (2013.01); *G01N 2223/053* (2013.01)

(58) Field of Classification Search
CPC ................. G01N 23/00; G01N 23/203; G01N 2223/053; G01N 23/04; B25J 9/02; A61B 5/103; A61B 5/107; A61B 6/483
USPC ............................. 378/70, 76, 87, 204, 205
See application file for complete search history.

(56) References Cited

U.S. PATENT DOCUMENTS

| | | | |
|---|---|---|---|
| 9,562,866 B2 * | 2/2017 | Morton | G01N 23/203 |
| 9,846,257 B2 | 12/2017 | Chen et al. | |
| 9,846,258 B2 | 12/2017 | Chen et al. | |
| 2011/0051886 A1 * | 3/2011 | Basu | G01N 23/046 |
| | | | 378/8 |

(Continued)

FOREIGN PATENT DOCUMENTS

| | | |
|---|---|---|
| CN | 104062688 A | 9/2014 |
| CN | 104133251 A | 11/2014 |

(Continued)

OTHER PUBLICATIONS

Office Action dated Apr. 19, 2018 for Chinese Patent Application No. 201610634464.7, which corresponds in priority to above-identified subject U.S. application.

*Primary Examiner* — Jurie Yun
(74) *Attorney, Agent, or Firm* — Knobbe, Martens, Olson & Bear, LLP (57) ABSTRACT

An autonomously mobile backscatter detection apparatus and method is disclosed. In one aspect, the apparatus includes a mobile platform configured to move freely in a horizontal plane. The apparatus further includes a backscatter detection imaging apparatus, arranged on the mobile platform, configured to acquire an image of an item to be inspected.

9 Claims, 7 Drawing Sheets (56) References Cited

U.S. PATENT DOCUMENTS

2015/0247946 A1    9/2015   Garretson et al.

FOREIGN PATENT DOCUMENTS

| CN | 205898713   | 1/2017  |
|----|-------------|---------|
| GB | 2519241 A   | 4/2015  |
| JP | 2001315080 A| 11/2001 |

* cited by examiner

AUTONOMOUSLY MOBILE BACKSCATTER DETECTION APPARATUS AND METHOD, AND POSITIONING METHOD FOR THE APPARATUS

RELATED APPLICATION

Any and all priority claims identified in the Application Data Sheet, or any correction thereto, are hereby incorporated by reference under 37 CFR 1.57. This application claims priority to Chinese Patent Application No. 201610634464.7, filed on Aug. 4, 2016, which is incorporated herein by reference in its entirety.

BACKGROUND

Technological Field

Embodiments of the disclosed technology generally relate to a field of safety inspection, and more particularly, to an autonomously mobile backscatter detection apparatus, an autonomously mobile backscatter detection method, and a positioning method for an autonomously mobile backscatter detection apparatus.

Description of the Related Technology

Safety inspection is a necessary procedure for frontier, customs, airport and other places. The safety inspection is mainly implemented to check whether there are dangerous items such as firearms, ammunition, explosive, corrosive and toxic radioactive materials in goods or baggage items, to ensure that entry or boarding of the items is not harmful. Therefore, the safety inspection is an important preventive measure to guarantee safety.

Backscatter detection technology is a kind of commonly used safety inspection technology, and has been extensively developed. However, conventional backscatter detection apparatuses are arranged in a fixed structure. As a result, the items to be inspected can only be detected at a fixed site or location, and it is necessary for them to pass through a scanning region of the backscatter detection apparatus, for example by means of a conveyor belt, to carry out the detection. In the case that the item to be inspected is a relatively large and heavy box, it is very difficult to carry or move it to the conveyor belt and convey it on the conveyor belt, resulting in difficulty in implementing the safety inspection. Moreover, it is required, for such a fixed backscatter detection apparatus, that the items to be inspected are regularly placed to carry out the detection. Even though the items have been placed on the conveyor belt, it is necessary for the items to be placed in such a manner that they can be better imaged by the backscatter detection apparatus. If not, it will lead to reduced imaging quality and reduced detection accuracy. Therefore, for irregularly, disorderly stored items to be inspected, the conventional fixed backscatter detection apparatus cannot carry out the detection.

The imaging quality of the backscatter detection apparatus is related to a distance between the apparatus and the item to be inspected, irradiation intensity, and other factors. If the items to be inspected of different sizes and different placements pass through the scanning region of the backscatter detection apparatus, it is necessary to adjust the distance between the apparatus and the respective item to be inspected and the irradiation intensity, so as to achieve a better imaging quality. In this aspect, the fixed backscatter detection apparatus cannot adjust the above-described distance and the irradiation intensity, especially the fixed backscatter detection apparatus cannot be dynamically adjusted according to needs for the imaging quality.

SUMMARY OF CERTAIN INVENTIVE ASPECTS

An objective of the disclosed technology is to provide an autonomously mobile backscatter detection apparatus capable of implementing safe inspection at variable sites and locations, so as to overcome at least one of defects in conventional inspection systems. A second objective is to provide an autonomously mobile backscatter detection apparatus capable of safely inspecting bulky, difficult to carry items. A third objective of the disclosed technology is to provide an autonomously mobile backscatter detection apparatus capable of safely inspecting irregular shaped or disorderly stored items. A fourth objective of the disclosed technology is to provide an autonomously mobile backscatter detection apparatus capable of being dynamically adjusted according to needs for the imaging quality, so as to obtain high quality detection. A fifth objective of the disclosed technology is to provide an autonomously mobile backscatter detection method and a positioning method for an autonomously mobile backscatter detection apparatus, capable of achieving the above objects.

One aspect is an autonomously mobile backscatter detection apparatus. The apparatus includes a backscatter detection imaging apparatus and a mobile platform, the backscatter detection imaging apparatus being arranged on the mobile platform, the mobile platform being configured to move freely in a horizontal plane.

In an embodiment, the mobile platform is a wheeled or tracked mobile platform.

In an embodiment, the mobile platform includes a chassis having a slip configuration. In an embodiment, the mobile platform further includes two sets of servo mechanisms. In an embodiment, the mobile platform is a two-wheeled or double-tracked mobile platform. In an embodiment, the two sets of servo mechanisms are configured to respectively drive two wheels or tracks of the mobile platform independently of each other.

In an embodiment, the mobile platform is provided with a servo mechanism encoder for feeding back a distance by which the wheels or tracks travel.

In an embodiment, the backscatter detection imaging apparatus is configured to move vertically or horizontally on the mobile platform by a set of servo mechanisms.

In an embodiment, the servo mechanism includes an elevator driven by a motor.

In an embodiment, the backscatter detection imaging apparatus is configured to scan from bottom to top, from top to bottom, from left to right or from right to left.

In an embodiment, a pulse width modulation control is performed on a movement of the backscatter detection imaging apparatus by a main control unit of the mobile platform.

In an embodiment, the mobile platform is configured to provide the backscatter detection imaging apparatus with electric power, and/or the mobile platform is configured to provide the backscatter detection imaging apparatus with computing and processing capacity.

In an embodiment, the autonomously mobile backscatter detection apparatus is configured to autonomously move the backscatter detection imaging apparatus and/or the mobile platform according to imaging quality, so as to adjust a distance between the backscatter detection imaging apparatus and an item to be inspected.

In an embodiment, the autonomously mobile backscatter detection apparatus is configured to autonomously move the backscatter detection imaging apparatus and/or the mobile platform according to scattering angles at a receiving end of the backscatter detection imaging apparatus, so as to adjust a distance between the receiving end and an item to be inspected.

In an embodiment, the autonomously mobile backscatter detection apparatus is configured to autonomously adjust an irradiation intensity of the backscatter detection imaging apparatus according to imaging quality, so as to ensure optimal imaging quality.

In an embodiment, the mobile platform is configured to move along a given path such that the backscatter detection imaging apparatus sequentially scans a plurality of items to be inspected.

In an embodiment, the autonomously mobile backscatter detection apparatus is configured to detect a gap between the items to be inspected so as to determine a boundary of the item to be inspected, and configured to move the backscatter detection imaging apparatus and/or the mobile platform to be in an orientation close to a center of the item to be inspected, which is determined according to the boundary.

In an embodiment, the mobile platform is provided with a laser ranging module, and position and distance information of points to be measured within a range of angles less than or equal to 270° in front of the mobile platform are acquired by rotating the laser ranging module.

In an embodiment, the mobile platform is provided with a memory for storing information necessary for an operation of the autonomously mobile backscatter detection apparatus.

Another aspect is a backscatter detection method for an autonomously mobile backscatter detection apparatus. The method includes determining a contour curve of a plurality of items to be inspected by a trajectory tracking control algorithm in a Cartesian coordinate system. The method further includes forming a trajectory curve of the mobile platform according to the contour curve. The method further includes moving the mobile platform to be close to a first item to be inspected along the trajectory curve and controlling the backscatter detection imaging apparatus to scan the first item to be inspected, under a control of a main control unit of the mobile platform. The method further includes continuing to move the mobile platform along the trajectory curve, such that the backscatter detection imaging apparatus sequentially scans the plurality of items to be inspected.

In an embodiment, the step of determining the contour curve of the plurality of items to be inspected comprises includes positioning the mobile platform in place and rotating a laser ranging module of the mobile platform to obtain position and distance information of the items to be inspected within a range of angles less than or equal to 270° in front of the mobile platform. In an embodiment, the method includes obtaining effective data points of the items to be inspected through filtering by a processor, and then calculating a contour curve function of the plurality of items to be inspected in the Cartesian coordinate system by the processor based on the data points.

In an embodiment, the method further includes detecting a gap between the items to be inspected so as to distinguish different items to be inspected and recording a position of the gap.

In an embodiment, the method further includes calculating an optimal scanning distance according to scattering angles and an area of a receiving end of the backscatter detection imaging apparatus after detecting the gap between the items to be inspected.

In an embodiment, the method further includes moving the backscatter detection imaging apparatus on the mobile platform vertically or horizontally, so as to scan the items to be inspected in an optimal imaging quality.

In an embodiment, the backscatter detection imaging apparatus is configured to scan from bottom to top, from top to bottom, from left to right or from right to left.

In an embodiment, a pulse width modulation control is performed on a movement of the backscatter detection imaging apparatus by a main control unit of the mobile platform.

In an embodiment, the method further comprises a step of: autonomously moving the backscatter detection imaging apparatus and/or the mobile platform according to imaging quality, so as to adjust a distance between the backscatter detection imaging apparatus and the item to be inspected.

In an embodiment, the method further includes autonomously moving the backscatter detection imaging apparatus and/or the mobile platform according to scattering angles at a receiving end of the backscatter detection imaging apparatus, so as to adjust a distance between the receiving end and the item to be inspected.

In an embodiment, the method further includes autonomously adjusting an irradiation intensity of the backscatter detection imaging apparatus according to imaging quality, so as to ensure optimal imaging quality.

In an embodiments, the method further includes detecting a gap between the items to be inspected so as to determine a boundary of the item to be inspected, and moving the backscatter detection imaging apparatus and/or the mobile platform to be in an orientation close to a center of the item to be inspected, which is determined according to the boundary.

Another aspect is a positioning method for the autonomously mobile backscatter detection apparatus. The method includes moving the mobile platform to a location where a plurality of feature points are capable of being detected, and collecting the plurality of feature points. The method further includes stopping moving the mobile platform, and observing the collected feature points to determine whether the feature points are stationary or not, so as to select the stationary feature points. The method further includes establishing a Cartesian coordinate system with a current position of a reference point on the mobile platform as an origin point and a front face of the mobile platform facing towards a X-axis positive direction, and calculating and recording coordinates of the plurality of feature points in the Cartesian coordinate system. The method further includes delimiting a first positioning area where three or more feature points are capable of being simultaneously observed by the mobile platform and a second positioning area other than the first positioning area. The method further includes determining a position of the mobile platform by a three-point positioning algorithm when the mobile platform is located in the first positioning area, and determining the position of the mobile platform by an servo mechanism encoder of the mobile platform when the mobile platform is located in the second positioning area.

In an embodiment, the selected stationary feature points comprises 5-10 feature points.

In an embodiment, if the number of the selected stationary feature points is less than 5, then the positioning method controls the mobile platform to move to a new location, and collects and selects feature points again.

In an embodiment, the feature points comprise wall corners, pillars or door frames.

In an embodiment, determining the position of the mobile platform by the three-point positioning algorithm includes rotating a laser ranging module of the mobile platform to respectively measure distances between the mobile platform and three feature points, and determining the position of the mobile platform based on the distances and the recorded coordinates of the three feature points.

In an embodiment, determining the position of the mobile platform by the servo mechanism encoder of the mobile platform includes feeding back a distance by which a wheel or a track travels through two servo motor encoders operated independently of each other, so as to calculate a position and an attitude angle of the mobile platform by a main control unit of the mobile platform.

In an embodiment, the position determined by the three-point positioning algorithm is used to replace the position determined by the servo mechanism encoder to eliminate accumulative error, when the mobile platform is located in the first positioning area.

According to embodiments of the disclosed technology, the backscatter detection imaging apparatus is placed on the mobile platform, thus the safety inspection can be carried out at variable sites and locations. The backscatter detection apparatus may be moved to the item to be inspected, thus it is unnecessary to move bulky and/or difficult to convey items. Moreover, the detection is carried out in a state where the items are irregularly placed, thus it can reduce the requirements for the placing manner of the items. The autonomously mobile backscatter detection apparatus can autonomously adjust a distance between the backscatter detection imaging apparatus and the item to be inspected, and an irradiation intensity of the backscatter detection imaging apparatus according to imaging quality. Therefore, it can ensure obtaining an optimal imaging quality and provide an accurate detection. In addition to the above advantages, embodiments of the disclosed technology also achieve accurate positioning of the autonomously mobile backscatter detection apparatus, and reduce the occurrence of accumulative errors.

For purposes of summarizing the disclosure, certain aspects, advantages and novel features of the innovations have been described herein. It is to be understood that not necessarily all such advantages may be achieved in accordance with any particular embodiment. Thus, the innovations may be embodied or carried out in a manner that achieves or optimizes one advantage or group of advantages as taught herein without necessarily achieving other advantages as may be taught or suggested herein.

DETAILED DESCRIPTION OF CERTAIN EMBODIMENTS

The following detailed description of certain embodiments presents various descriptions of specific embodiments. However, the innovations described herein can be embodied in a multitude of different ways, for example, as defined and covered by the claims. In this description, reference is made to the drawings where like reference numerals can indicate identical or functionally similar elements. It will be understood that elements illustrated in the figures are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings.

Figure 1:
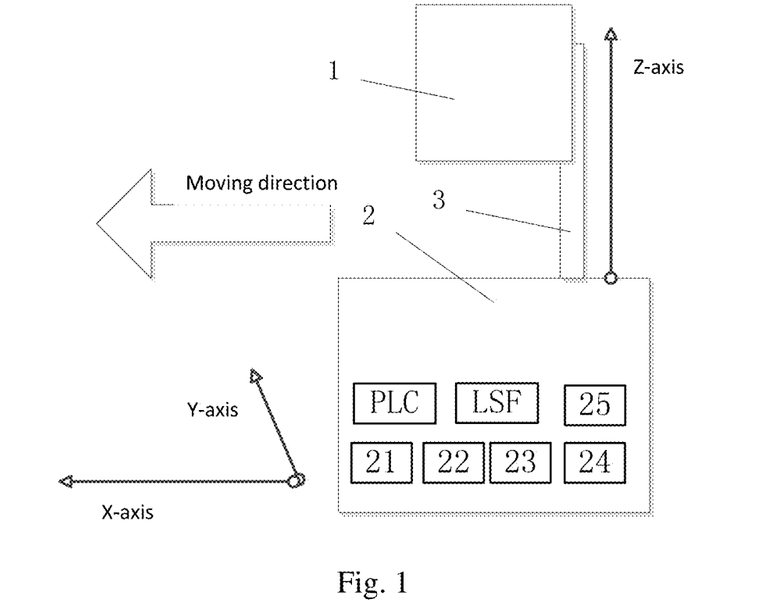
FIG. 1 is a schematic structural view of an autonomously mobile backscatter detection apparatus according to an embodiment of the disclosed technology.
Figure 2:
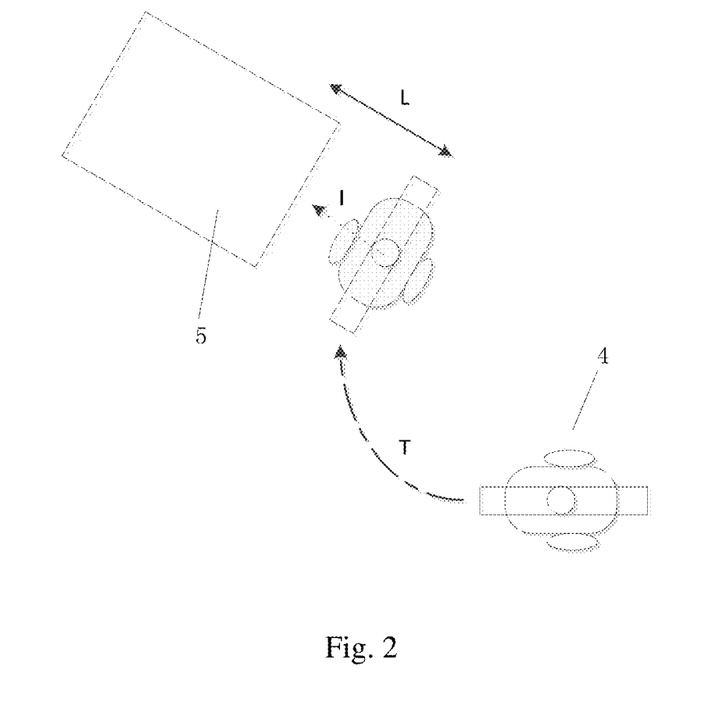
FIG. 2 is a schematic view showing a scanning quality control process of the autonomously mobile backscatter detection apparatus.

FIGS. 1 and 2 includes an autonomously mobile backscatter detection apparatus 4, including a backscatter detection imaging apparatus 1 and a mobile platform 2. The backscatter detection imaging apparatus 1 is arranged on the mobile platform 2, and the mobile platform 2 is configured to move freely in a horizontal plane x-y. The mobile platform 2 provides the backscatter detection imaging apparatus 1 with electric power and/or computing and processing capacity. As shown in FIG. 1, the backscatter detection imaging apparatus 1 may be moved vertically along z-axis on the mobile platform 2 by a set of servo mechanisms. In an alternative embodiment, the backscatter detection imaging apparatus 1 may also be moved in a horizontal direction. In the embodiment shown in FIG. 1, the servo mechanism is an elevator 3 driven by a motor. It should be noted that the backscatter detection imaging apparatus may be configured to scan from bottom to top, from top to bottom, from left to right or from right to left, which is not intended to be limited herein.

In an embodiment, the mobile platform 2 may be a wheeled or tracked mobile platform, and a chassis 21 of the mobile platform 2 has a slip configuration. The mobile platform 2 includes two sets of servo mechanisms 22. The mobile platform 2 is a two-wheeled or double-tracked mobile platform. The two sets of servo mechanisms 22 respectively drive two wheels or tracks 23 of the mobile platform independently of each other. The mobile platform 2 includes a servo mechanism encoder 24 for feeding back a distance by which the wheels or tracks 23 travel. The mobile platform 2 includes a main control unit, for example, main controller PLC. A pulse width modulation (PWM) control is performed on a movement of the backscatter detection imaging apparatus 1 by the main control unit PLC of the mobile platform 2. The mobile platform 2 includes a laser ranging module (LSF) which can be rotated to measure the distance to objects at different angles.

FIG. 2 shows a scanning quality control process implemented by the autonomously mobile backscatter detection apparatus 4. The backscatter detection apparatus 4 travels along a given path T to the vicinity of an item 5 to be inspected, and performs a backscatter detection on the item 5 to be inspected. The autonomously mobile backscatter detection apparatus 4 autonomously moves the backscatter detection imaging apparatus 1 and/or the mobile platform 2 according to imaging quality, so as to adjust a distance L between the backscatter detection imaging apparatus 1 and the item 5 to be inspected. Alternatively or additionally, the autonomously mobile backscatter detection apparatus 4 autonomously moves the backscatter detection imaging apparatus 1 and/or the mobile platform 2 according to scattering angles at a receiving end of the backscatter detection imaging apparatus, so as to adjust a distance between the receiving end and the item 5 to be inspected. In addition, the autonomously mobile backscatter detection apparatus 4 may also be configured to autonomously adjust an irradiation intensity of the backscatter detection imaging apparatus 1 according to imaging quality, so as to ensure optimal imaging quality. After one item 5 to be inspected has been scanned, the mobile platform 2 is moved to the next item 5 to be inspected along the given path T, such that the backscatter detection imaging apparatus 1 sequentially scans a plurality of items 5 to be inspected.

In an embodiment, the autonomously mobile backscatter detection apparatus 4 is configured to detect a gap between the items 5 to be inspected to determine a boundary of the item to be inspected, and configured to move the backscatter detection imaging apparatus 1 and/or the mobile platform 2 to be in an orientation close to a center of the item 5 to be inspected, which is determined according to the boundary.

Figure 3:
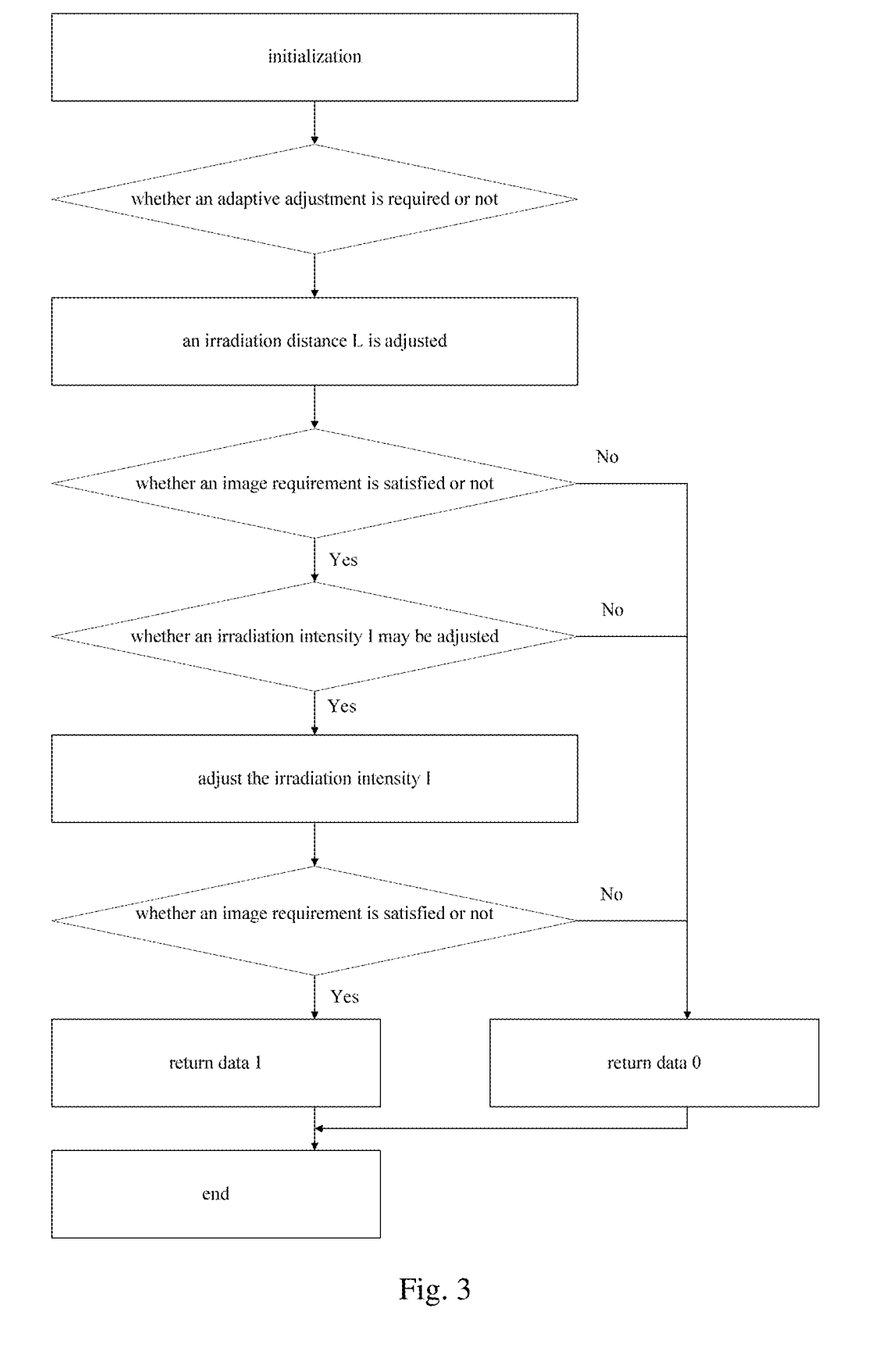
FIG. 3 is a flowchart showing the scanning quality control process of the autonomously mobile backscatter detection apparatus.

FIG. 3 shows a flowchart of the scanning quality control process of the autonomously mobile backscatter detection apparatus 4. First the backscatter detection apparatus 4 is initialized. After the initialization, it is determined whether an adaptive adjustment is required or not. If the adaptive adjustment is required, then an irradiation distance L between the backscatter detection imaging apparatus 1 and the item to be inspected 5 is adjusted. After the adjustment of the irradiation distance L, it is determined whether an image requirement is satisfied or not. If the image requirement is not satisfied, then data returns to 0. Otherwise it is determined whether an irradiation intensity I may be adjusted. If the irradiation intensity I cannot be adjusted, then the data returns to 0. Otherwise the irradiation intensity I is adjusted. Next, it is determined whether the image requirement is satisfied or not. If the image requirement is not satisfied, then the data returns to 0. Otherwise the data returns to 1. Finally the control process is ended.

Further, the mobile platform 2 includes a laser ranging module (LSF), and position and distance information of points to be measured within a range of angles less than or equal to 270° in front of the mobile platform can be obtained by rotating the laser ranging module LSF. The mobile platform 2 is provided with a memory for storing information necessary for an operation of the autonomously mobile backscatter detection apparatus 4.

One aspect of the disclosed technology is a backscatter detection method for the autonomously mobile backscatter detection apparatus 4. The method includes determining a contour curve f(x) of a plurality of items 5 to be inspected by a trajectory tracking control algorithm in a Cartesian coordinate system. The method further includes forming a trajectory curve t(x) of the mobile platform 2 according to the contour curve. The method further includes moving the mobile platform 2 to be close to a first item 5 to be inspected along the trajectory curve and controlling the backscatter detection imaging apparatus 1 to scan the first item 5 to be inspected, under a control of a main control unit of the mobile platform 2. The method further includes continuing to move the mobile platform 2 along the trajectory curve, such that the backscatter detection imaging apparatus 1 sequentially scans the plurality of items 5 to be inspected. In an example, the step of determining the contour curve of the plurality of items 5 to be inspected includes positioning the mobile platform 2 in place and rotating a laser ranging module of the mobile platform 2 to obtain position and distance information of the items 5 to be inspected within a range of angles less than or equal to 270° in front of the mobile platform 2, obtaining effective data points of the items to be inspected through filtering operation by a processor 25 (optionally, an ARM processor), and then calculating a contour curve function f(x) of the plurality of items 5 to be inspected in the Cartesian coordinate system by the processor based on the data points. The main control unit PLC generates a corresponding trajectory curve function t(x) based on the contour curve function, such that the point in the trajectory curve function t(x) is spaced apart from the corresponding point in the contour curve function f(x) by a distance d, where d is approximately equal to the distance between the backscatter detection imaging apparatus 1 and the item (box) 5 to be inspected.

During implementing the backscatter detection method for the autonomously mobile backscatter detection apparatus 4, the method further comprises a step of detecting a gap between the items 5 to be inspected to distinguish different items 5 to be inspected and recording a position of the gap. An optimal scanning distance is calculated according to scattering angles and an area of the receiving end of the backscatter detection imaging apparatus 1 after detecting the gap between the items 5 to be inspected.

In an embodiment, the backscatter detection method further includes moving the backscatter detection imaging apparatus 1 on the mobile platform 2 vertically or horizontally, so as to scan the items 5 to be inspected in an optimal imaging quality. Additionally, the backscatter detection imaging apparatus 1 may be configured to scan from bottom to top, from top to bottom, from left to right or from right to left.

In an embodiment, the mobile platform 2 includes a main control unit PLC, and a pulse width modulation control is performed on a movement of the backscatter detection imaging apparatus 1 by the main control unit PLC of the mobile platform 2. The backscatter detection method further includes moving the backscatter detection imaging apparatus 1 and/or the mobile platform 2 autonomously according to imaging quality, so as to adjust a distance between the backscatter detection imaging apparatus 1 and the item 5 to be inspected. Alternatively or additionally, the method further includes moving the backscatter detection imaging apparatus 1 and/or the mobile platform 2 autonomously according to scattering angles at a receiving end of the backscatter detection imaging apparatus, so as to adjust a distance between the receiving end and the item 5 to be inspected. In an embodiment, the backscatter detection method further includes adjusting an irradiation intensity of the backscatter detection imaging apparatus 1 autonomously according to imaging quality, so as to ensure optimal imaging quality. Optionally, the backscatter detection method further comprises a step of: detecting a gap between the items to be inspected so as to determine a boundary of the item to be inspected, and moving the backscatter detection imaging apparatus and/or the mobile platform to be in an orientation close to a center of the item to be inspected, which is determined according to the boundary.

Figure 4:
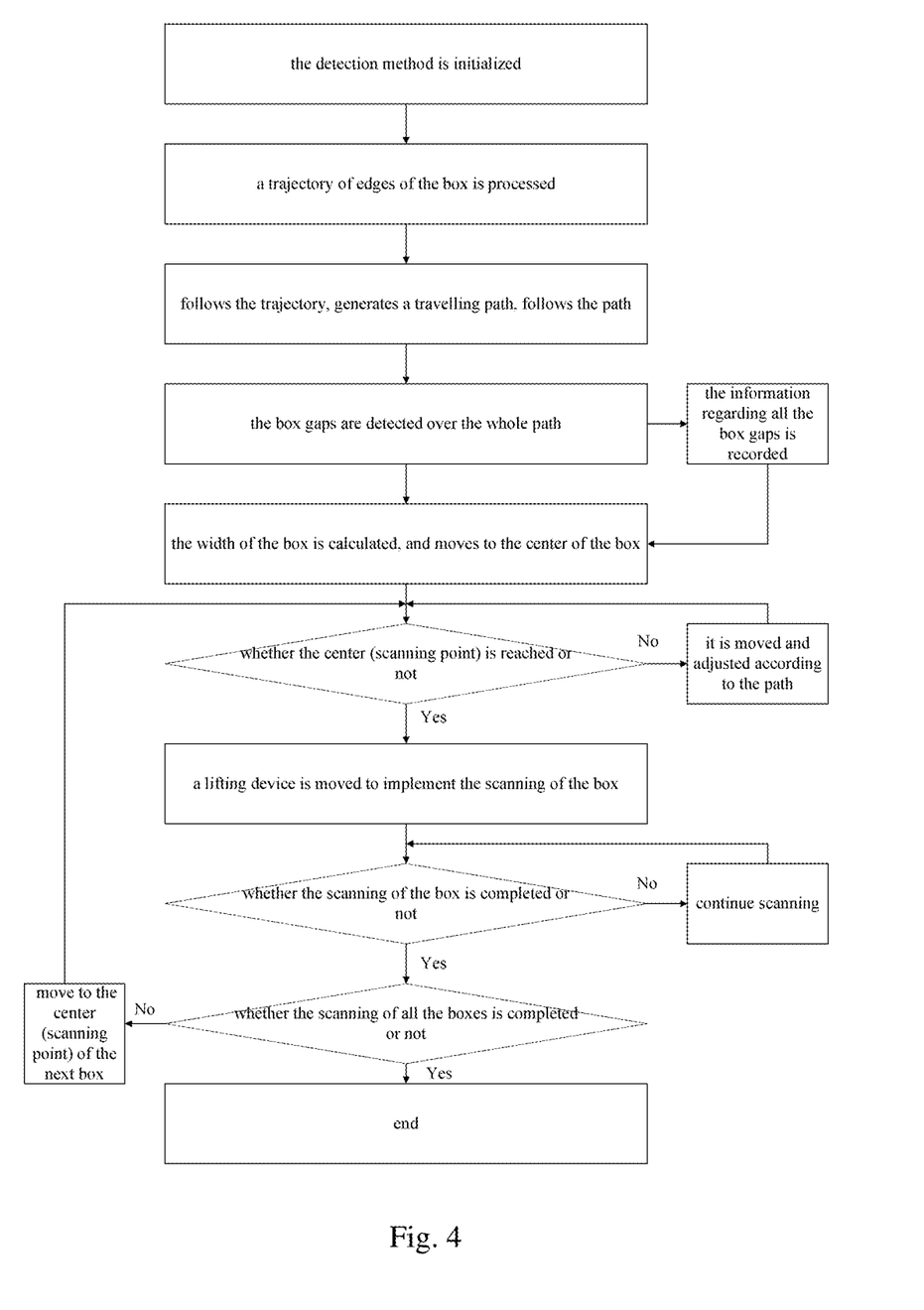
FIG. 4 is a flowchart of an autonomously mobile backscatter detection method according to an embodiment of the disclosed technology.

Next, an operation process of the autonomously mobile backscatter detection method according to an embodiment of the disclosed technology will be described in detail, taking a goods box as an example, with reference FIG. 4.

First, the detection method is initialized. Then, a trajectory of edges of the box is processed to form a contour curve of a plurality of boxes. Next, following the trajectory, a travelling path of the mobile platform 2 is generated. The mobile platform 2 follows the path. Next, gaps between the boxes are detected over the whole path, and the information regarding all gaps between the boxes is recorded. The width of the box is calculated according to the information regarding the gaps between the boxes, and the mobile platform 2 is moved to a position close to the center of the box. Next, it is determined whether the center (scanning point) is reached or not. If not, then the mobile platform 2 is moved and adjusted according to the path and after that it is determined whether the center is reached or not. If so, then a lifting device (for example, the elevator 3) is moved to implement the scanning of the box. Next, it is determined whether the scanning of the box is completed or not. If the scanning of the box is not completed, then the scanning of the box continues. Otherwise it is determined whether the scanning of all the boxes is completed or not. If the scanning of all the boxes is completed, then the operation process ends. Otherwise the mobile platform 2 moves to the center (scanning point) of the next box and all the steps after the step of "determining whether the center (scanning point) is reached or not" are repeated.

Figure 5:
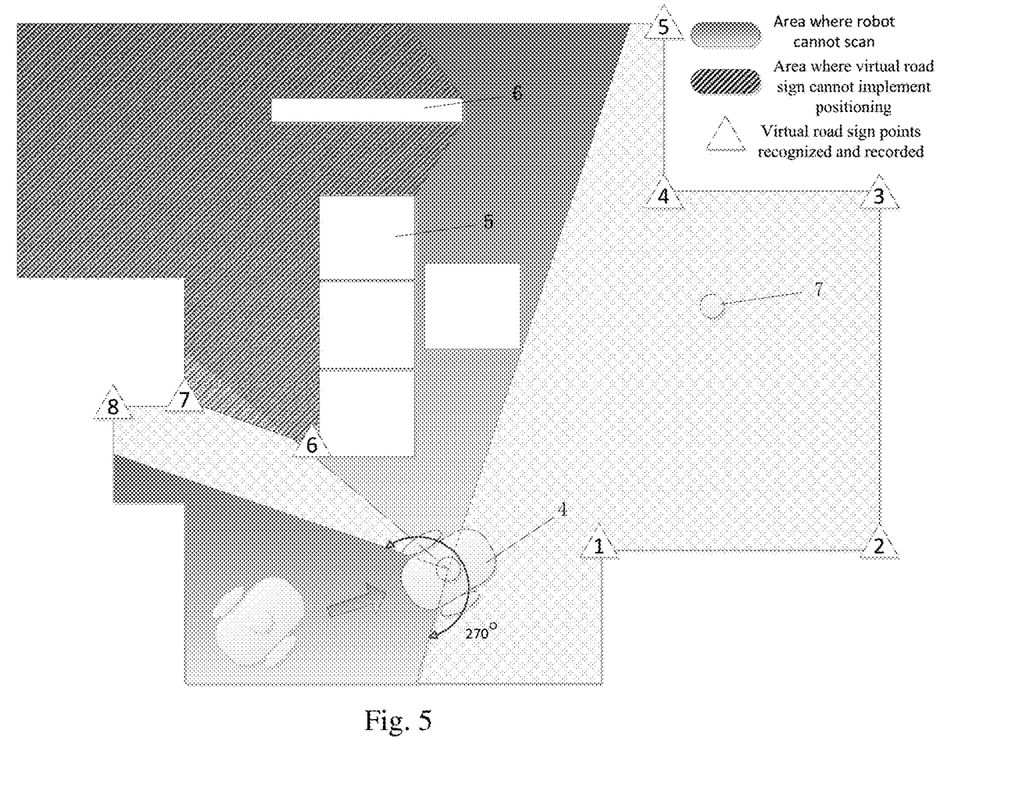
FIG. 5 is a schematic view of a positioning area.

Another aspect of the disclosed technology is a positioning method for the autonomously mobile backscatter detection apparatus 4. The method includes moving the mobile platform 2 to a location where a plurality of feature points are capable of being detected. The method further includes collecting the plurality of feature points (in the embodiment shown in FIG. 5, the feature points include virtual road sign points 1-8). The method further includes stopping moving the mobile platform 2, observing the collected feature points, and determining whether the feature points are stationary or not, so as to select the stationary feature points. The method further includes establishing a Cartesian coordinate system with a current position of a reference point on the mobile platform 2 as an origin point (0, 0), and a front direction of the mobile platform as a X-axis positive direction, calculating coordinates of the plurality of feature points in the Cartesian coordinate system, and recording the coordinates (x1, y1), (x2, y2), (x3, y3) of the plurality of feature points. The method further includes delimiting a first positioning area where three or more feature points are capable of being simultaneously observed by the mobile platform and a second positioning area excluding the first positioning area (as shown in FIG. 5, the area where the virtual road sign cannot be used to implement positioning is the second positioning area); and determining a position of the mobile platform 2 by a three-point positioning algorithm when the mobile platform 2 is located in the first positioning area. The method further includes determining the position of the mobile platform 2 by an servo mechanism encoder of the mobile platform 2 when the mobile platform 2 is located in the second positioning area.

In the positioning method, as shown in FIG. 5, in order to collect the feature points (generally wall corners, pillars or the like), the backscatter detection apparatus 4 (robot) is firstly autonomously moved to a proper location so as to cover a wide range of feature points; then 5-10 stationary feature points are selected; if the number of the selected stationary feature points is less than 5, then the positioning method controls to move the mobile platform 2 to a new location, and collect and select the feature points again. In the embodiment shown in FIG. 5, the observing area includes obstacles 6 and pillars 7. In the illustrated location, the backscatter detection apparatus 4 can recognize and record the virtual road sign points 1-8 as the feature points. The feature points may comprise wall corners, pillars or door frames.

The step of determining the position of the mobile platform 2 by the three-point positioning algorithm includes rotating a laser ranging module of the mobile platform 2 to measure distances (r1, r2, r3) between the mobile platform 2 and three respective feature points, and determining the position of the mobile platform 2 based on the distances and the recorded coordinates (x1, y1), (x2, y2), (x3, y3) of the three feature points. The step of determining the position of the mobile platform 2 by the servo mechanism encoder of the mobile platform 2 includes feeding back a distance by which a wheel or a track travels through two servo motor encoders operated independently of each other, so as to calculate a position and an attitude angle of the mobile platform 2 by a main control unit of the mobile platform 2. The position determined by the three-point positioning algorithm is used to replace the position determined by the servo mechanism encoder to eliminate accumulative error, when the mobile platform 2 is located in the first positioning area.

Figure 6:
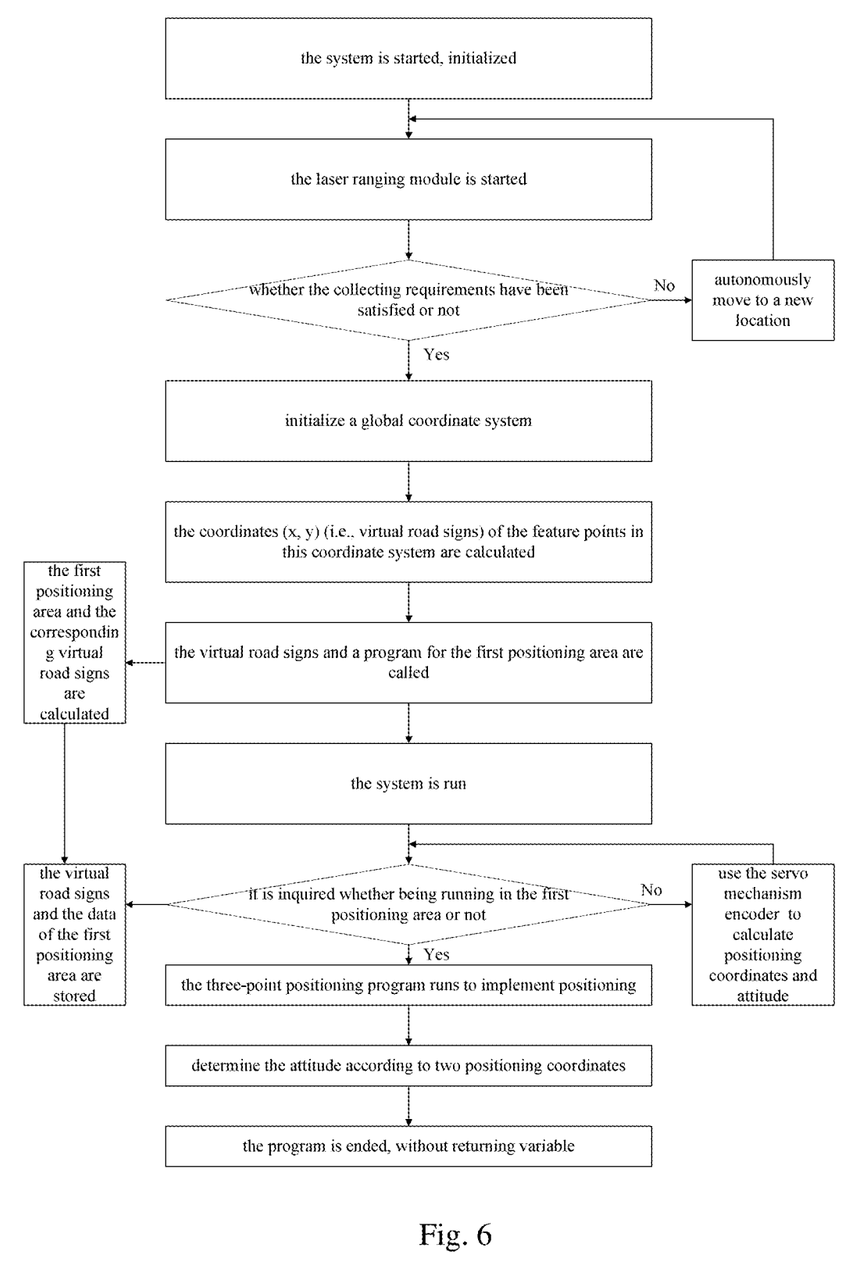
FIG. 6 is a flowchart showing a positioning process of the autonomously mobile backscatter detection apparatus.

Next, a positioning process of the autonomously mobile backscatter detection apparatus 4 will be described with reference to FIG. 6. First, the system is started and initialized. Next the laser ranging module (LSF) is started to determine whether the requirements for collecting feature points have been satisfied or not. If the requirements are not satisfied, then the mobile platform 2 is autonomously moved to a new location and the laser ranging module is restarted. If the requirements are satisfied, then a global coordinate system is initialized; the coordinates (x, y) (i.e., virtual road signs) of the feature points in this coordinate system are calculated. The virtual road signs and a program for the first positioning area are called, as shown in FIG. 6, so as to determine the first positioning area and the corresponding virtual road signs, and the virtual road signs and the data of the first positioning area are stored. Simultaneously the system is run to inquire whether the mobile platform 2 is running in the first positioning area or not. If not, then the servo mechanism encoder (a drive wheel encoder) is used to calculate positioning coordinates and attitude. If yes, then the three-point positioning program runs to implement positioning and determine the attitude according to two positioning coordinates. Next, the program is ended without returning variables.

Figure 7:
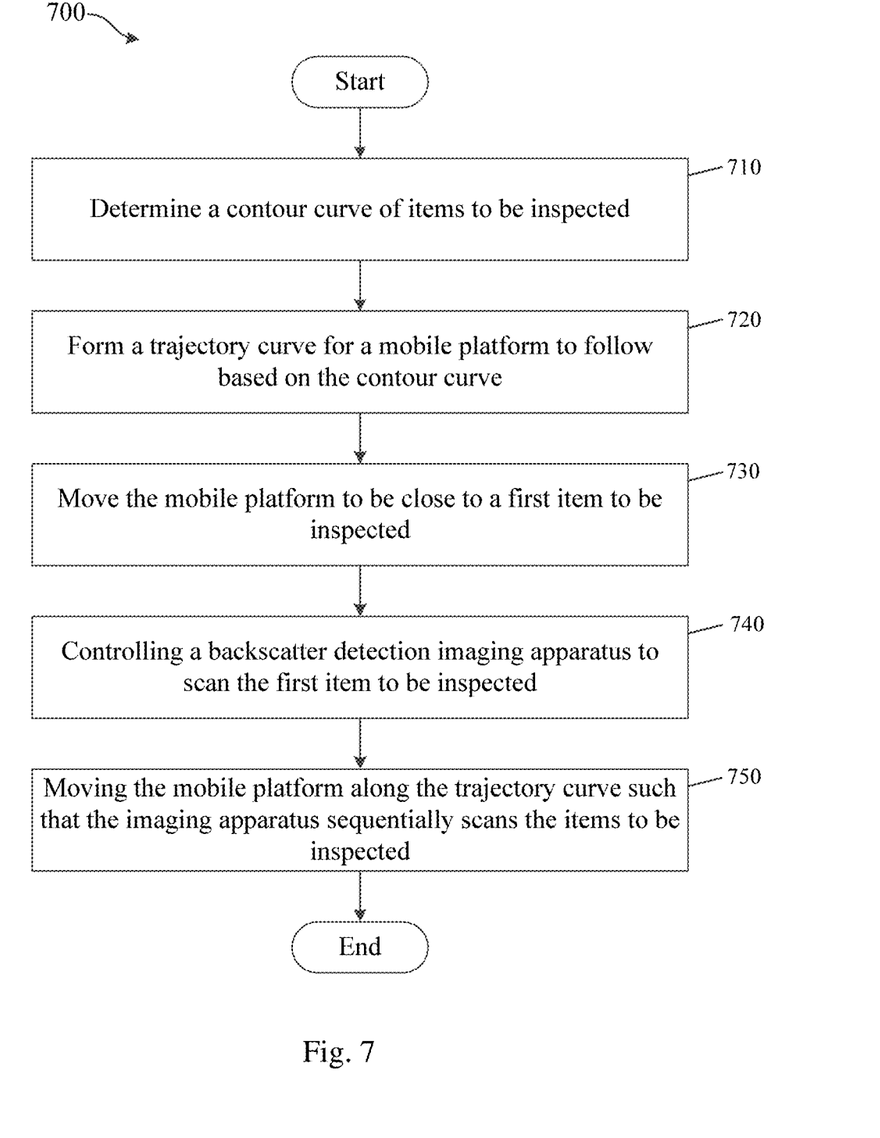
FIG. 7 is a flowchart of a method of backscatter detection for an autonomously mobile backscatter detection apparatus according to an embodiment of the disclosed technology.

FIG. 7 is a flowchart of a method 700 of backscatter detection for an autonomously mobile backscatter detection apparatus according to an embodiment of the disclosed technology. In an embodiment, at least some of the functionality of method 700 is performed by the backscatter detection imaging apparatus 1, mobile platform 2, elevator 3, chassis 21, servo mechanisms 22, wheels or tracks 23, servo mechanism encoders 24, processor 25, main controller PLC, laser range finder LSF, and/or autonomously mobile backscatter detection apparatus 4 to inspect item 5, as depicted in FIGS. 1 and 2.

In block 710, method 700 determines a contour curve of a plurality of items to be inspected, by a trajectory tracking control algorithm in a Cartesian coordinate system. In block 720, method 700 forms a trajectory curve of the mobile platform according to the contour curve. In block 730, method 700 moves the mobile platform to be close to a first item to be inspected along the trajectory curve. In block 740, method 700 controls the backscatter detection imaging apparatus to scan the first item to be inspected, under a control of a main control unit of the mobile platform. In block 750, method 700 moves the mobile platform along the trajectory curve, such that the backscatter detection imaging apparatus sequentially scans the plurality of items to be inspected.

Figure 8:
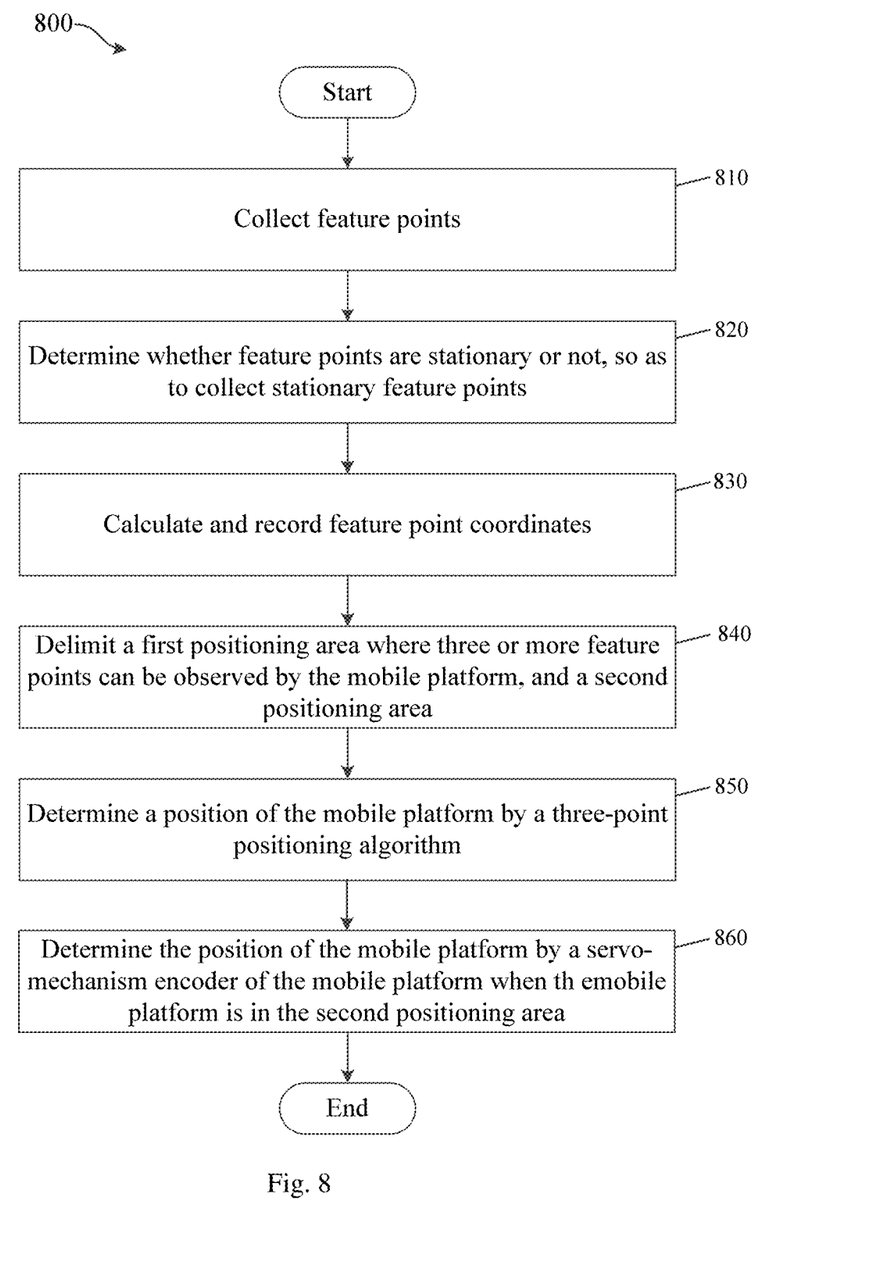
FIG. 8 is a flowchart of a method of positioning an autonomously mobile backscatter detection apparatus according to an embodiment of the disclosed technology.

FIG. 8 is a flowchart of a method 800 of positioning an autonomously mobile backscatter detection apparatus according to an embodiment of the disclosed technology. In an embodiment, at least some of the functionality of method 800 is performed by the backscatter detection imaging apparatus 1, mobile platform 2, elevator 3, chassis 21, servo mechanisms 22, wheels or tracks 23, servo mechanism encoders 24, processor 25, main controller PLC, laser range finder LSF, and/or autonomously mobile backscatter detection apparatus 4 to inspect item 5, as depicted in FIGS. 1 and 2.

In block 810, method 800 moves the mobile platform to a location where feature points are capable of being detected, and collects the feature points. In block 820, method 820 stops the mobile platform from moving, and observes the collected feature points to determine whether the feature points are stationary or not, so as to select the stationary feature points. In block 830, method 800 establishes a Cartesian coordinate system with a current position of a reference point on the mobile platform as an origin point and a front face of the mobile platform facing towards a X-axis positive direction, and calculates and records coordinates of the plurality of feature points in the Cartesian coordinate system. In block 840, method 800 delimits a first positioning area where three or more feature points are capable of being simultaneously observed by the mobile platform, and a second positioning area other than the first positioning area. In block 850, method 800 determines a position of the mobile platform by a three-point positioning algorithm when the mobile platform is located in the first positioning area. In block 860, method 800 determines the position of the mobile platform by a servo mechanism encoder of the mobile platform when the mobile platform is located in the second positioning area.

While various exemplary embodiments of the disclosed technology have been shown and described, it will be understood by those skilled in the art that changes and modifications may be made to these embodiments without departing from the principle and spirit of the disclosed technology, and the scope of the disclosed technology is defined by the appended claims and their equivalents.

The various features and processes described herein may be implemented independently of one another, or may be combined in various ways. All possible combinations and sub combinations are intended to fall within the scope of this disclosure. In addition, certain methods or process blocks may be omitted in some implementations. The methods and processes disclosed herein are also not limited to any particular sequence, and the blocks or states relating thereto can be performed in any other sequences that are appropriate. For example, described blocks or states may be performed in an order other than that specifically disclosed, or multiple blocks or states may be combined in a single block or state. The example blocks or states may be performed in serial, in parallel, or in some other manner as appropriate. Blocks or states may be added to or removed from the disclosed example embodiments as suitable. The example systems and components described herein may be configured differently than described. For example, elements may be added to, removed from, or rearranged compared to the disclosed example embodiments. Various embodiments can apply different techniques for fabricating different types of electronic devices.

While certain embodiments have been described, these embodiments have been presented by way of example only, and are not intended to limit the scope of the disclosure. Indeed, the novel devices, systems, apparatus, methods, and systems described herein may be embodied in a variety of other forms; furthermore, various omissions, substitutions and changes in the form of the methods and systems described herein may be made without departing from the spirit of the disclosure. For example, while blocks are presented in a given arrangement, alternative embodiments may perform similar functionalities with different components and/or circuit topologies, and some blocks may be deleted, moved, added, subdivided, combined, and/or modified. Each of these blocks may be implemented in a variety of different ways. Any suitable combination of the elements and acts of the various embodiments described above can be combined to provide further embodiments.

What is claimed is:

1. A method of backscatter detection for an autonomously mobile backscatter detection apparatus,
wherein the autonomously mobile backscatter detection apparatus comprises:
a mobile platform configured to move freely in a horizontal plane; and
a backscatter detection imaging apparatus, arranged on the mobile platform and configured to acquire an image of an item of two items to be inspected,
and wherein the method comprises:
determining a contour curve of a plurality of items to be inspected by a trajectory tracking control algorithm in a Cartesian coordinate system;
forming a trajectory curve of the mobile platform according to the contour curve;
moving the mobile platform to be close to a first item to be inspected along the trajectory curve;
controlling the backscatter detection imaging apparatus to scan the first item to be inspected, under a control of a main control unit of the mobile platform; and
moving the mobile platform along the trajectory curve, such that the backscatter detection imaging apparatus sequentially scans the plurality of items to be inspected,
wherein the method further comprises:
detecting a gap between the items to be inspected so as to distinguish different items to be inspected and recording a position of the gap, and moving the backscatter detection imaging apparatus and/or the mobile platform to be in an orientation close to a center of one of the items to be inspected, which is determined according to boundaries of the one of the items to be inspected.

2. The method according to claim 1, wherein the step of determining the contour curve of the plurality of items to be inspected comprises:
positioning the mobile platform in place and rotating a laser ranging module of the mobile platform to obtain position and distance information of the items to be inspected within a range of angles less than or equal to 270° in front of the mobile platform,
obtaining effective data points of the items to be inspected through filtering by a processor, and
then calculating a contour curve function of the plurality of items to be inspected in the Cartesian coordinate system by the processor based on the data points.

3. The method according to claim 2, further comprising a step of: calculating an optimal scanning distance according to scattering angles and an area of a receiving end of the backscatter detection imaging apparatus after detecting the gap between the items to be inspected.

4. The method according to claim 1, further comprising a step of: moving the backscatter detection imaging apparatus on the mobile platform vertically or horizontally, so as to scan the items to be inspected in an optimal imaging quality.

5. A method of positioning an autonomously mobile backscatter detection apparatus,
wherein the autonomously mobile backscatter detection apparatus comprises:
a mobile platform configured to move freely in a horizontal plane; and
a backscatter detection imaging apparatus, arranged on the mobile platform and configured to acquire an image of an item of two items to be inspected,
and wherein the method comprises:
moving the mobile platform to a location where a plurality of feature points are capable of being detected, and finding the plurality of feature points;
stopping the mobile platform, and observing the found feature points to determine whether the feature points are stationary or not, so as to select the stationary feature points;
establishing a Cartesian coordinate system with a current position of a reference point on the mobile platform as an origin point and a front face of the mobile platform facing towards a X-axis positive direction, and calculating and recording coordinates of the plurality of feature points in the Cartesian coordinate system;
delimiting a first positioning area where three or more feature points are capable of being simultaneously observed by the mobile platform and a second positioning area other than the first positioning area;
determining a position of the mobile platform by a three-point positioning algorithm when the mobile platform is located in the first positioning area, and
determining the position of the mobile platform by a servo mechanism encoder of the mobile platform when the mobile platform is located in the second positioning area.

6. The method according to claim 5, wherein the selected stationary feature points comprise 5-10 feature points, and if the number of the selected stationary feature points is less than 5, then the positioning method controls the mobile platform to move to a new location, and finds and selects feature points again.

7. The method according to claim 5, wherein the step of determining the position of the mobile platform by the three-point positioning algorithm comprises: rotating a laser ranging module of the mobile platform to respectively measure distances between the mobile platform and three feature points, and determining the position of the mobile platform based on the distances and the recorded coordinates of the three feature points.

8. The method according to claim 5, wherein the step of determining the position of the mobile platform by the servo mechanism encoder of the mobile platform comprises: feeding back a distance by which a wheel or a track travels through two servo motor encoders operated independently of each other, so as to calculate a position and an attitude angle of the mobile platform by a main control unit of the mobile platform.

9. The method according to claim 5, wherein the position determined by the three-point positioning algorithm is used to replace the position determined by the servo mechanism encoder to eliminate accumulative error, when the mobile platform is located in the first positioning area.

\* \* \* \* \*